(12) United States Patent
Baturin et al.

(10) Patent No.: US 9,494,534 B2
(45) Date of Patent: Nov. 15, 2016

(54) MATERIAL DIFFERENTIATION WITH PHASE CONTRAST IMAGING

(71) Applicant: Carestream Health, Inc., Rochester, NY (US)

(72) Inventors: Pavlo Baturin, Rochester, NY (US); Mark E. Shafer, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 166 days.

(21) Appl. No.: 14/499,762

(22) Filed: Sep. 29, 2014

(65) Prior Publication Data

US 2015/0092916 A1 Apr. 2, 2015

Related U.S. Application Data

(60) Provisional application No. 61/884,159, filed on Sep. 30, 2013.

(51) Int. Cl.
*G01N 23/20* (2006.01)

(52) U.S. Cl.
CPC .............................. *G01N 23/20075* (2013.01)

(58) Field of Classification Search
CPC .. A61B 6/484; A61B 6/4291; A61B 6/4035; A61B 6/4233
See application file for complete search history.

(56) References Cited

U.S. PATENT DOCUMENTS

| 2010/0220834 A1* | 9/2010 | Heismann ............. A61B 6/032 378/19 |
| 2014/0177789 A1 | 6/2014 | Shafer et al. |
| 2014/0185746 A1 | 7/2014 | Baturin et al. |
| 2014/0185896 A1 | 7/2014 | Baturin et al. |

OTHER PUBLICATIONS

Commonly assigned U.S. Appl. No. 61/939,925, entitled: Method and Apparatus for Fabrication and Tuning of Grating-Based Differential Phase Contrast Imaging System filed on Feb. 14, 2014, by Baturin et al.
Commonly assigned U.S. Appl. No. 14/143,183, entitled: Phase Retrieval From Differential Phase Contrast Imaging filed on Dec. 30, 2013, by Baturin et al.
Commonly assigned U.S. Appl. No. 61/892,490, entitled: Surrogate Phantom for Differential Phase Contrast Imaging filed on Oct. 18, 2013, by Baturin et al.
Commonly assigned U.S. Appl. No. 14/143,254, entitled: Large FOV Phase Contrast Imaging Based on Detuned Configuration Including Acquisition and Reconstruction Techniques filed on Dec. 30, 2013, by Baturin et al.

* cited by examiner

*Primary Examiner* — Hoon Song

(57) ABSTRACT

A method and system to determine material composition of an object comprises capturing a series of digital radiographic images of the object using a single exposure energy level. An intensity of the captured images is determined as well as phase shift differences. A difference in material composition of the object may be determined based on a combination of the determined intensity and the modulated phase shifts of the captured images.

20 Claims, 9 Drawing Sheets

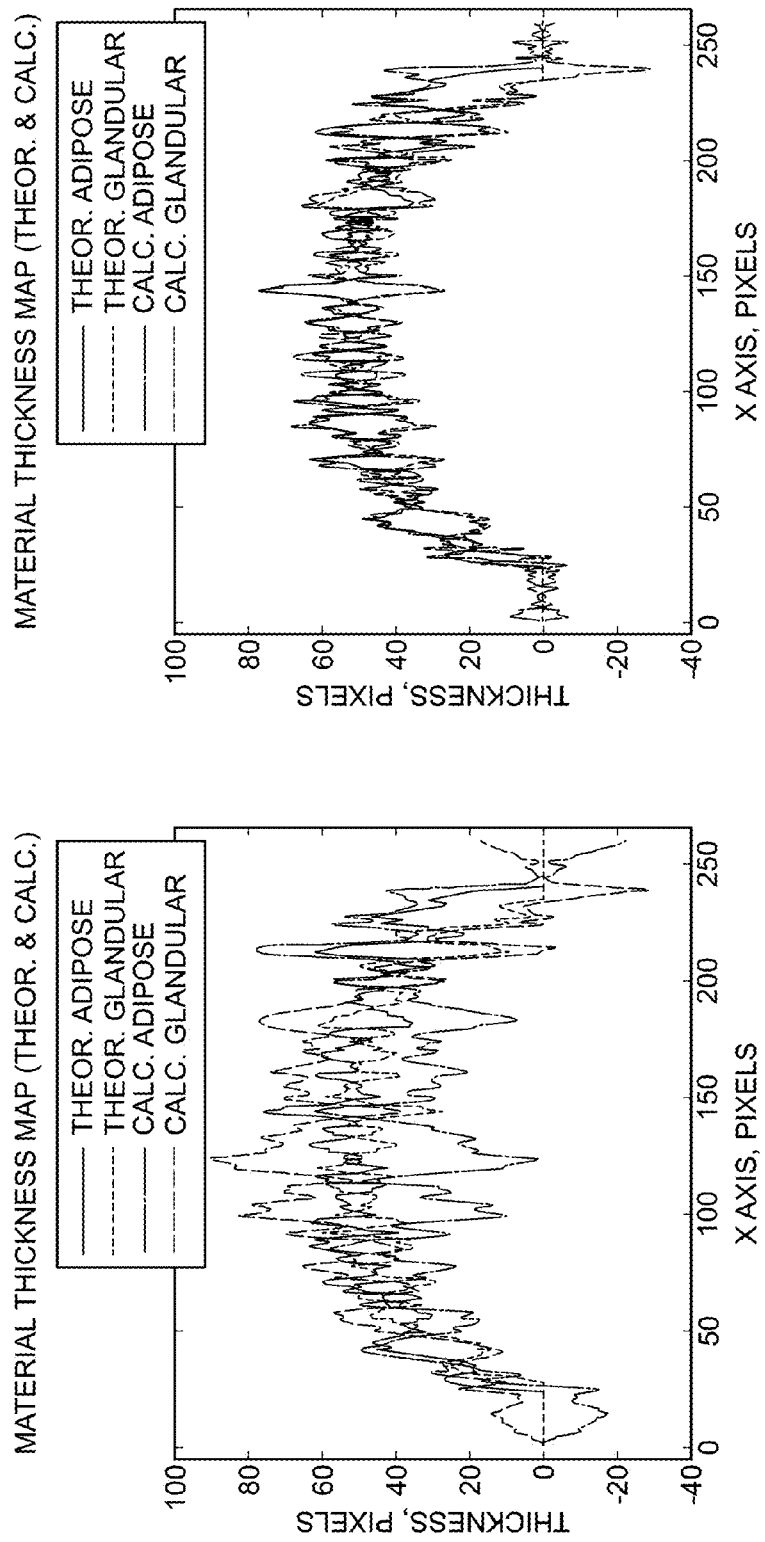

MATERIAL DIFFERENTIATION WITH PHASE CONTRAST IMAGING

CROSS REFERENCE TO RELATED APPLICATIONS

This application claims priority to U.S. Patent Application Ser. No. 61/884,159, filed Sep. 30, 2013, in the name of Baturin et al., and entitled BREAST DENSITY ASSESSMENT WITH PHASE CONTRAST IMAGING.

This application is related in certain respects to U.S. Patent Application Ser. No. 61/939,925, filed Feb. 14, 2014, in the name of Baturin et al., and entitled METHOD AND APPARATUS FOR FABRICATION AND TUNING OF GRATING-BASED DIFFERENTIAL PHASE CONTRAST IMAGING SYSTEM; U.S. patent application Ser. No. 14/143,183, filed Dec. 30, 2013, in the name of Baturin et al., and entitled PHASE RETRIEVAL FROM DIFFERENTIAL PHASE CONTRAST IMAGING; U.S. Patent Application Ser. No. 61/892,490, filed Oct. 18, 2013, in the name of Baturin et al., and entitled SURROGATE PHANTOM FOR DIFFERENTIAL PHASE CONTRAST IMAGING; U.S. patent application Ser. No. 14/143,254, filed Dec. 30, 2013, in the name of Baturin et al., and entitled LARGE FOV PHASE CONTRAST IMAGING BASED ON DETUNED CONFIGURATION INCLUDING ACQUISITION AND RECONSTRUCTION TECHNIQUES; U.S. patent application Ser. No. 13/732,767, filed Jan. 2, 2013, in the name of Baturin et al., and entitled CONDITIONAL LIKELIHOOD MATERIAL DECOMPOSITION AND METHODS OF USING THE SAME; U.S. patent application Ser. No. 13/729,443, filed Dec. 28, 2012, in the name of Baturin et al., and entitled SPECTRAL GRATING-BASED DIFFERENTIAL PHASE CONTRAST SYSTEM FOR MEDICAL RADIOGRAPHIC IMAGING; U.S. patent application Ser. No. 13/724,096, filed Dec. 21, 2012, in the name of Baturin et al., and entitled GRATING-BASED DIFFERENTIAL PHASE CONTRAST IMAGING SYSTEM WITH ADJUSTABLE CAPTURE TECHNIQUE FOR MEDICAL RADIOGRAPHIC IMAGING; all seven of which are incorporated herein by reference in their entirety.

BACKGROUND OF THE INVENTION

The subject matter disclosed herein generally relates to digital x-ray imaging methods and systems. In particular, to methods and systems for acquiring multiple image information of an object using a grating-based differential phase contrast imaging technique.

FIELD OF THE INVENTION

Material differentiation is an important task in the diagnostic medical imaging field. For example, discrimination between two or more soft tissue materials may be required to reconstruct 3D material morphology of an x-ray scanned object. The number of biomedical applications where material differentiation may be necessary is countless. As further examples, material identification may be necessary for i) identification of contrast materials such as iodine or others, e.g., gold nanoparticles, in cardiovascular imaging; ii) identification of cancerous tumors or assessment of breast density in digital mammography; and iii) identification of kidney stones in renal imaging. A dual energy technique is one of the modern methods allowing material differentiation, but requires a plurality of x-ray exposures, where at least one of the exposures may be taken at a "low" energy of the x-ray beam and another exposure may be taken at "high" energy setting. Alternatively, such a method may invoke a single x-ray scan with photon-counting energy-resolving detector, where the measurement of x-ray spectrum may be split by detector's comparators into energy bins, sometime referred to as "spectral" measurement. Since it may be desirable to minimize the number of x-ray exposures and because the photon-counting energy-resolving detectors are not yet clinically accessible, there may be a high need for development of a single scan based method or apparatus capable of differentiating between at least two or more different materials.

The discussion above is merely provided for general background information and is not intended to be used as an aid in determining the scope of the claimed subject matter.

BRIEF DESCRIPTION OF THE INVENTION

A method and system to determine material composition of an object comprises capturing a series of digital radiographic images of the object using a single exposure energy level. An intensity of the captured images may be determined as well as phase shift differences. A difference in material composition of the object may be determined based on a combination of the determined intensity and the modulated phase shifts of the captured images. An advantage that may be realized in the practice of some disclosed embodiments of the disclosed invention is an improved diagnostic image that may be obtained in a single scan.

In one embodiment, a method of determining material composition of an object is disclosed. The method comprises capturing a series of digital radiographic images of the object using an x-ray beam having a single energy magnitude. An intensity of the captured images are determined as well as determining a phase shift magnitude between the captured images of the object. A difference in material composition of the object may be determined based on a combination of the determined intensity and the determined phase shift of the captured images.

In another embodiment, a system, for determining material composition, comprises an x-ray source aimed at the object. A phase grating may be positioned behind the object and a moveable analyzer grating may be positioned behind the phase grating. A digital detector may be positioned behind the analyzer grating to capture a plurality of digital radiographic images of the object. A processing unit connected to the x-ray source and to the detector controls operations thereof.

These, and other, aspects and objects of the present invention will be better appreciated and understood when considered in conjunction with the following description and the accompanying drawings. It should be understood, however, that the following description, while indicating preferred embodiments of the present invention and numerous specific details thereof, is given by way of illustration and not of limitation. For example, the summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The figures below are intended to be drawn neither to any precise scale with respect to relative size, angular relationship, or relative position nor to any combinational relationship with respect to interchangeability, substitution, or representation of an actual implementation

BRIEF DESCRIPTION OF THE DRAWINGS

So that the manner in which the features of the invention may be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments, emphasis generally being placed upon illustrating the features of certain embodiments of the invention. In the drawings, like numerals are used to indicate like parts throughout the various views. Thus, for further understanding of the invention, reference may be made to the following detailed description, read in connection with the drawings in which.

Figure 6:
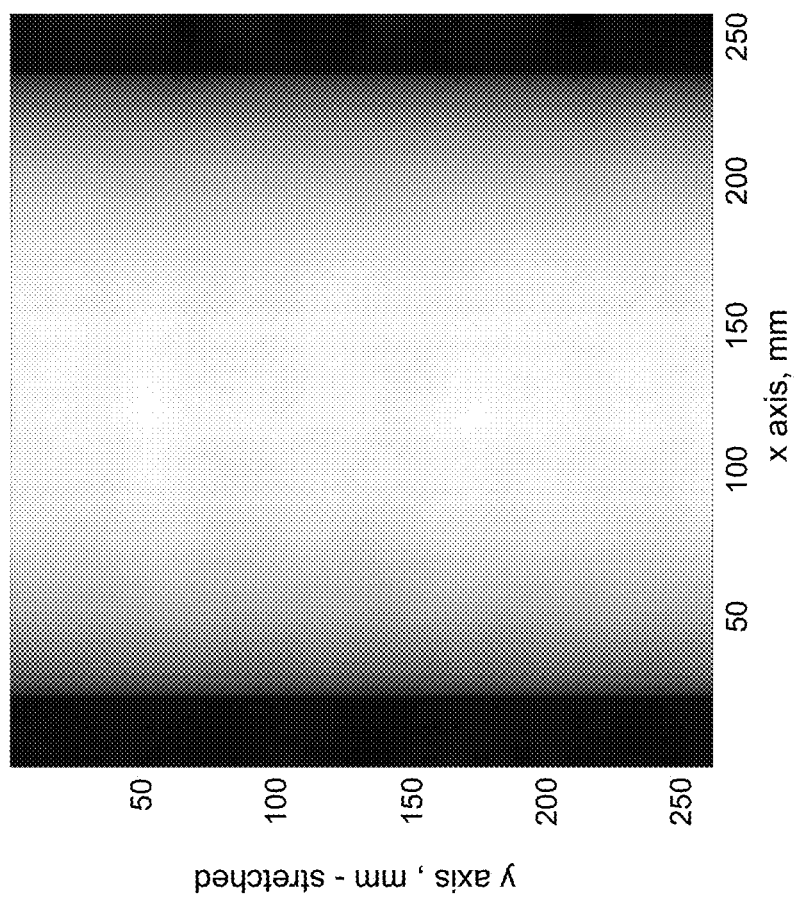

respectively;

FIG. 6 is an integrated phase shift image obtained by regularized integration of $$\frac{\partial (\varphi \cdot t)}{\partial x};$$

Figure 7B:
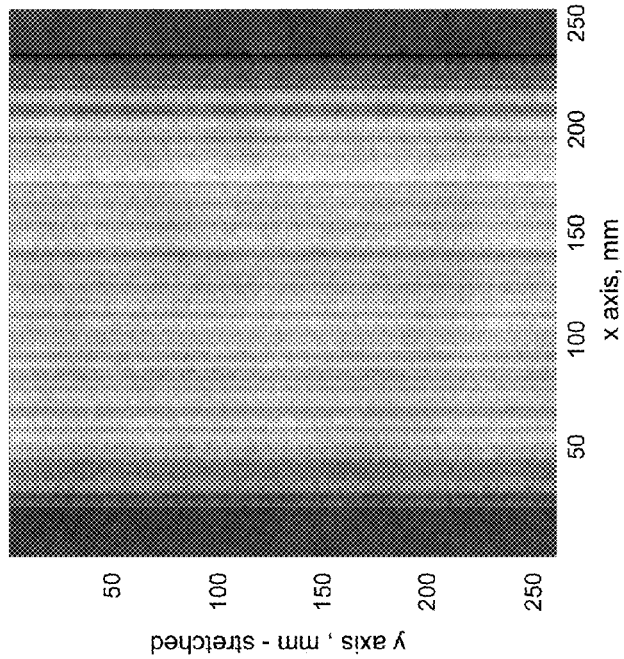
Figure 7A:
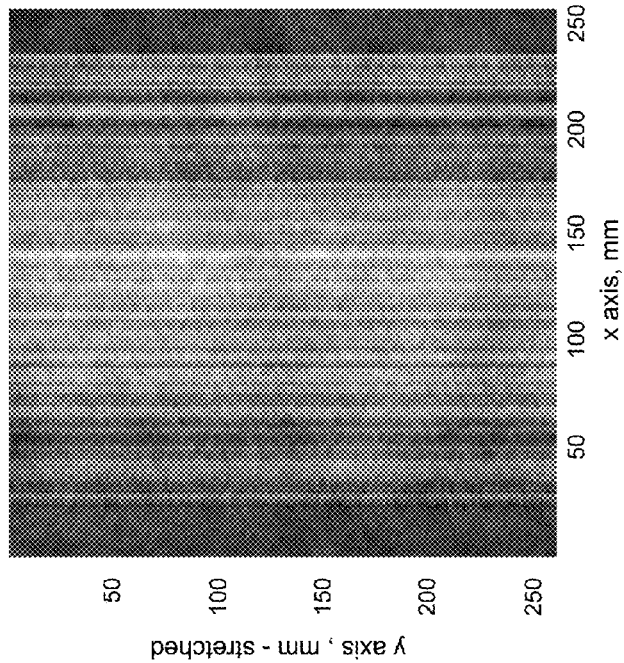
Figure 9:
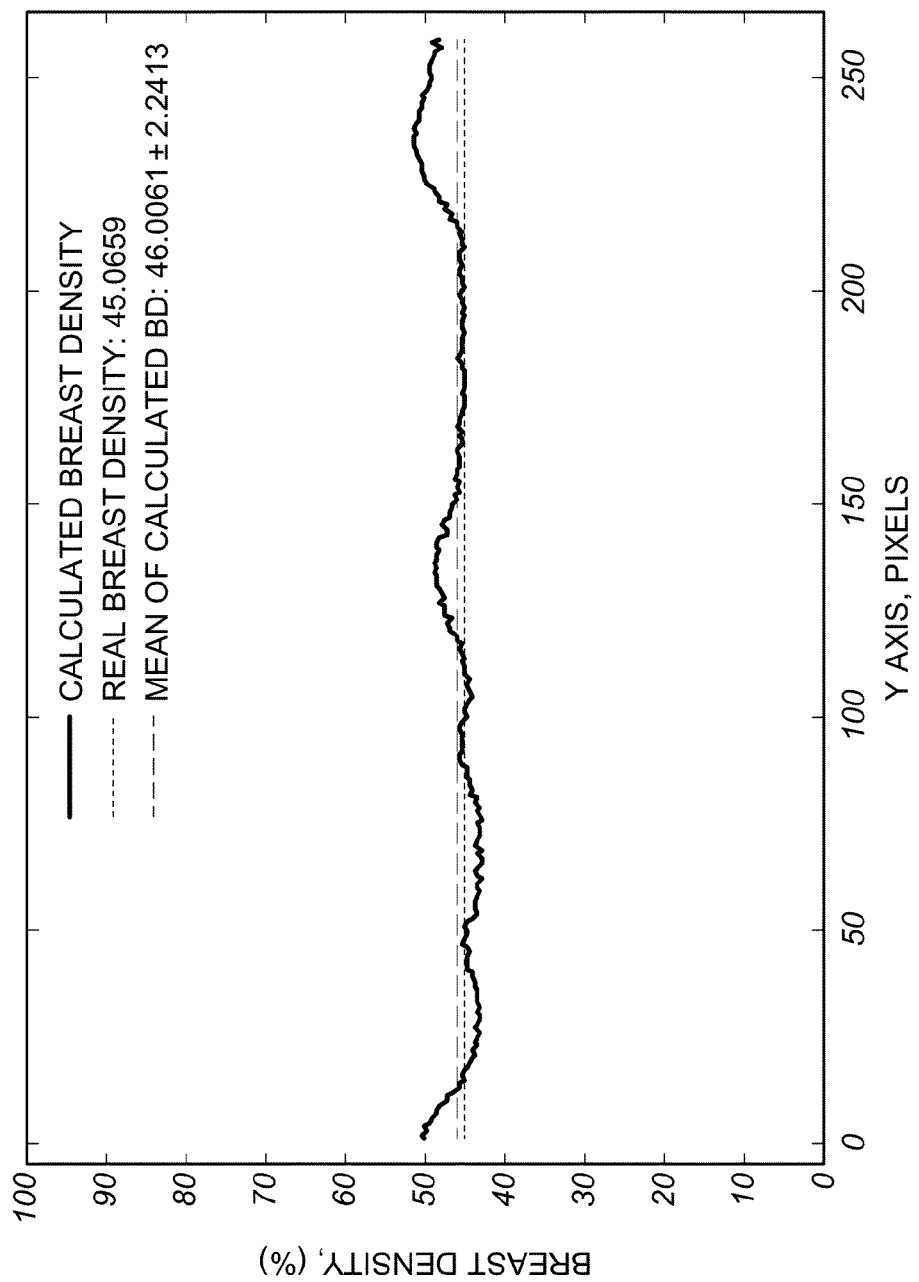

FIGS. 7A-B are reconstructed images of thickness maps for adipose tissue and glandular tissue, respectively;

FIGS. 8A-B are example profiles across the x direction for theoretical and calculated thickness values of adipose and glandular tissues; and FIG. 9 illustrates breast density as a function of y profile.

DETAILED DESCRIPTION OF THE INVENTION

Conventional medical diagnostic x-ray imaging devices rely on absorption properties of materials to provide the information about the interior structure of imaged objects. Such absorption type of imaging assumes non-refractive x-rays penetrating the object under study. The contrast is produced due to the differences in the absorption cross section. While generally good contrast between highly attenuating (hard) and weakly attenuating (soft) materials is observed, the differentiation between soft-tissue materials can be difficult due to a low relative contrast. For example, the low-contrast soft tissue materials including, but not limited to vessels, cartilages, lungs, and breast tissues provide poor contrast in comparison to highly attenuating bone structures. The problem of soft-tissue imaging may be addressed by interferometric x-ray imaging devices, which utilize the wave nature of x-ray radiation. Such imaging interferometers focus on measuring the refraction characteristics manifested in the process of x-rays passing through the object of study. In addition to absorption image these devices can provide differential phase contrast and dark-field images.

Figure 1A:
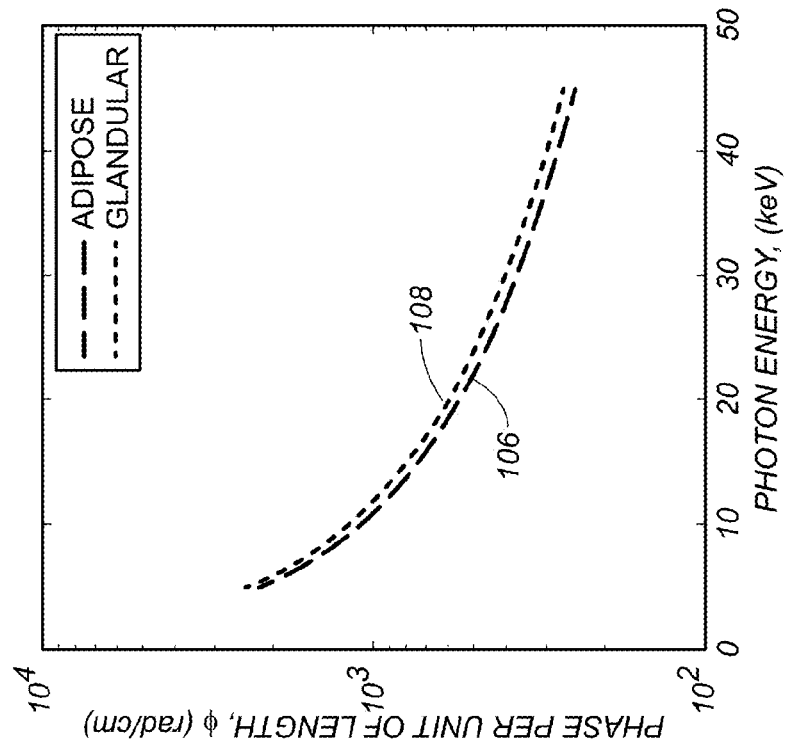
FIGS. 1A-B are exemplary calibration curves showing the linear attenuation and phase shift per unit of length for adipose and glandular tissues, respectively.
Figure 1B:
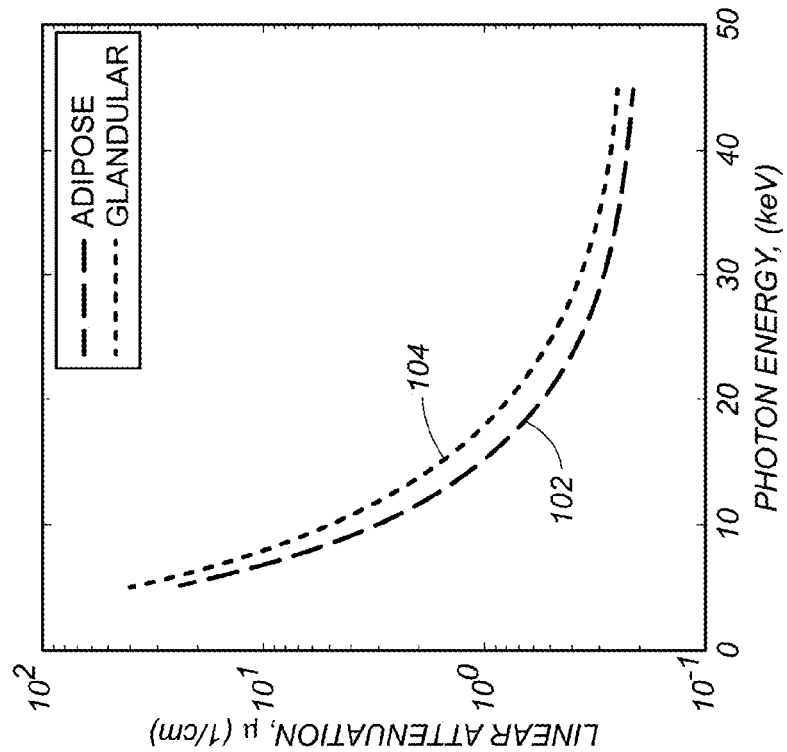

We will refer to differential phase contrast imaging technique herein as DPCI. Differential phase contrast images contain the information of x-ray phase shift properties through the object of study, i.e., similar to absorption imaging providing complementary knowledge of material properties. In contrast, dark-field image provides the information about the local scattering of the object, which will not be discussed herein in detail. One example of an object that may benefit from embodiments of the scanning and analysis invention disclosed herein is breast examination. The human female breast is primarily composed of two types of tissue: glandular and adipose. When an x-ray scan of the breast is performed, image data in the form of a projection detector voxel may contain any combination of these tissues. The total attenuation of the x-ray energy represented in a voxel may be expressed as a sum of attenuations through glandular and adipose tissues. The same statement is true for data representing phase shifts, which an x-ray beam experiences, of various magnitudes, when it is passing through an object. For an x-ray, passed through an adipose tissue of thickness $t_a$ and glandular tissue of thickness $t_g$, the total attenuation and phase shift may be written in the following way:

$$\begin{cases} \mu \cdot t = \mu_a \cdot t_a + \mu_g \cdot t_g \\ \varphi \cdot t = \varphi_a \cdot t_a + \varphi_g \cdot t_g \end{cases}, \quad (1)$$

where $t=t_a+t_g$ is the distance that the x-ray traveled in the object, where $\mu_a$ and $\mu_g$ are the linear attenuations per unit of length, and $\phi_a$ and $\phi_g$ are the phase shifts per unit of length, for the adipose and glandular tissues, respectively. These values are not only dependent on the tissue type, but also on the level of x-ray energy used. Both may be found by doing calibration runs with x-ray exposures at different mean energies and tabulating the measurements, and are generally known for particular medical images based on numerous accumulated data. Examples of such calibration runs are illustrates in the curves shown in FIGS. 1A-B, wherein FIG. 1A illustrates a calibration curve for linear attenuation per unit length (1/cm) of adipose tissue 102 and of glandular tissue 104; FIG. 1B illustrates a calibration curve for phase shift per unit length (rad/cm) of adipose tissue 106 and of glandular tissue 108. Although the plots in these graphs are simulated, one may experimentally measure attenuation and phase shift points at different mean energies and apply a fit (e.g., a polynomial fit) to obtain the calibration curves.

Exemplary method and system embodiments described herein are preferably independent of the phase contrast acquisition technique, although embodiments of the phase contrast acquisition will be described. Thus, any phase change acquisition technique (e.g., system or method) that results in absorption and phase shift images may be used. If differential phase contrast imaging technique is used, where absorption and differential phase images are retrieved, it is convenient to write a solution of equation (1) in the following form:

$$\begin{cases} t_a = \left(\frac{(\mu \cdot t)}{\mu_g} - \frac{1}{\varphi_g} \int \frac{\partial (\varphi \cdot t)}{\partial x} dx\right) \Big/ \left(\frac{\mu_a}{\mu_g} - \frac{\varphi_a}{\varphi_g}\right) \\ t_g = \left(\frac{(\mu \cdot t)}{\mu_a} - \frac{1}{\varphi_a} \int \frac{\partial (\varphi \cdot t)}{\partial x} dx\right) \Big/ \left(\frac{\mu_g}{\mu_a} - \frac{\varphi_g}{\varphi_a}\right) \end{cases} \quad (2)$$

Here $t_a$ and $t_g$ represent the thickness maps of adipose and glandular tissues, respectively. Total transmission $\mu \cdot t$ (also attenuation or absorption) and total differential phase shift $\partial(\phi \cdot t)/\partial x$ along a linear trajectory t may be measured during the scan, while $\mu$ and $\phi$ parameters for adipose and glandular tissues may be found from calibration as shown, for example, in FIGS. 1A-B. Thus, one form of the breast density BD may be calculated as:

$$BD = \frac{t_g}{t_a + t_g} \cdot 100\% \quad (3)$$

Simulation

1. Modeling of Absorption and Phase Shift in the Materials

The refractive index of an x-ray scanned material may be expressed as a complex number:

$$n = 1 - \delta + i\beta, \quad (4)$$

where the imaginary part $\beta$ contributes to the attenuation of the amplitude (absorption) and the real part $\delta$ (refraction index decrement) is responsible for the phase shift. When the x-ray is passing through the material, or object, the attenuation and phase shift may be calculated as:

$$\begin{cases} \mu(x, y) = \frac{4\pi}{\lambda} \int \beta(x, y, z) dz \\ \varphi(x, y) = \frac{2\pi}{\lambda} \int \delta(x, y, z) dz \end{cases} \quad (5)$$

For a material of density $\rho$ the refractive index may be expressed in terms of the atomic scattering factors $f_1$ and $f_2$:

$$n \cong 1 - \frac{r_e N_a \lambda^2 \rho}{2\pi} \left(\sum_k x_k (f_{1,k} + i f_{2,k})\right) \Big/ \left(\sum_k x_k A_k\right), \quad (6)$$

where $r_e$, $N_a$, $\lambda$, and $\rho$ are the electron radius, Avogadro number, photon wavelength, and effective density of the material, respectively. The summation may be taken over the relative concentrations $x_k$ of each of the chemical elements of atomic mass $A_k$ comprising the material. The calibration curves presented in FIG. 1 were estimated using equations (5) and (6).

2. Exemplary Differential Phase Contrast Imaging System

Figure 2:
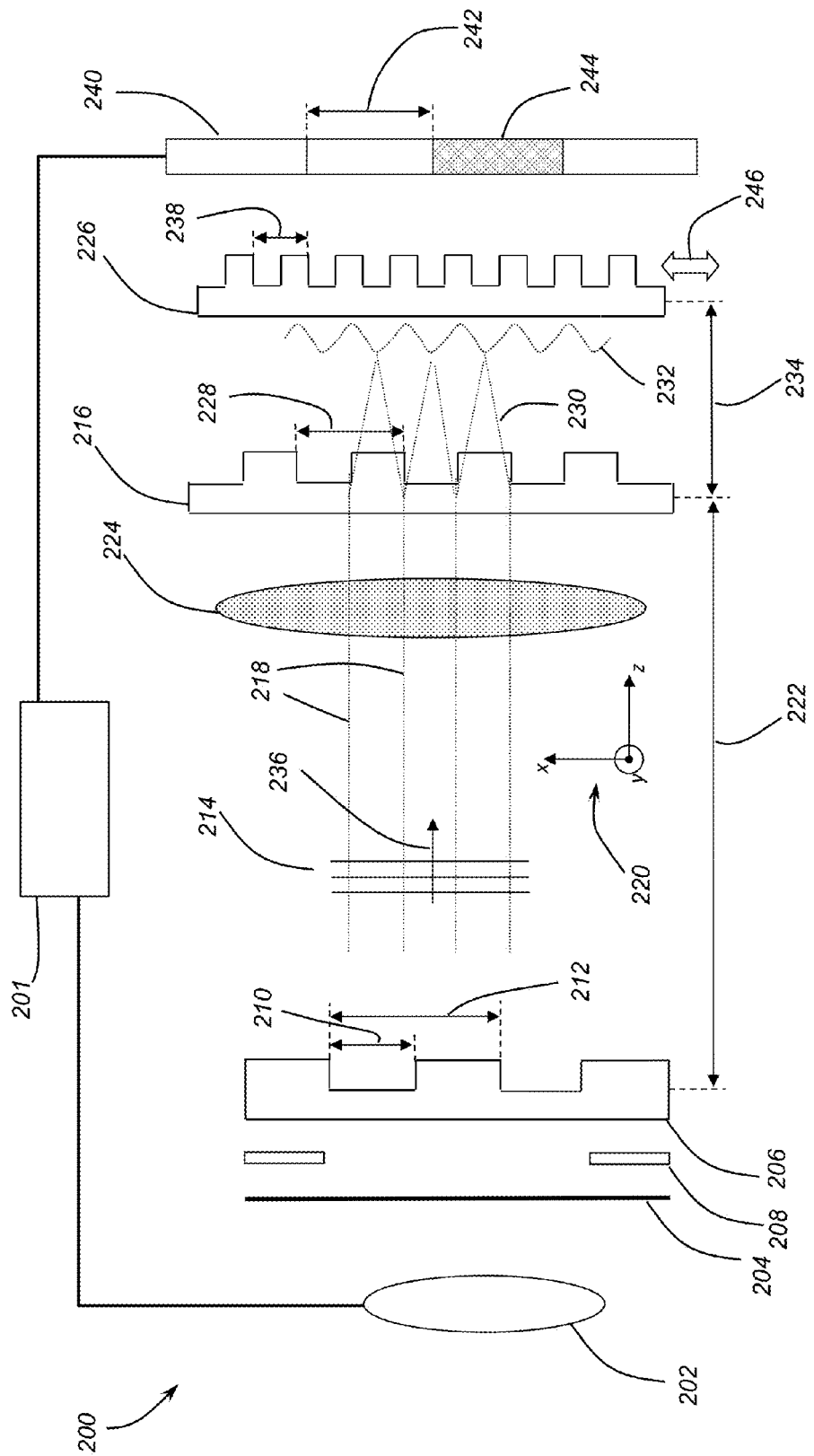
FIG. 2 is an exemplary schematic diagram of a three-grating PCI system that invokes a phase stepping technique for extraction of phase shift information.

As described herein, any phase contrast imaging technique, which provides absorption and phase shift information, may be used in the exemplary system and method embodiments in this application. The example of the three-grating differential phase contrast imaging apparatus 200, which may be used, is shown in FIG. 2. The phase stepping acquisition technique is illustrated as an example, although any other acquisition technique may be used instead. In this phase stepping technique, an analyzer grating 226 of the three gratings, 206, 216, 226 may be periodically stepped in one direction (up or down, in the perspective of FIG. 2) as indicated by arrow 246 which is referenced herein as the x direction using the coordinate system 220. The grating 226 may be stepped over a total distance 238 with respect to the remainder of the gratings 206, 216, which may be kept stationary.

Figure 3:
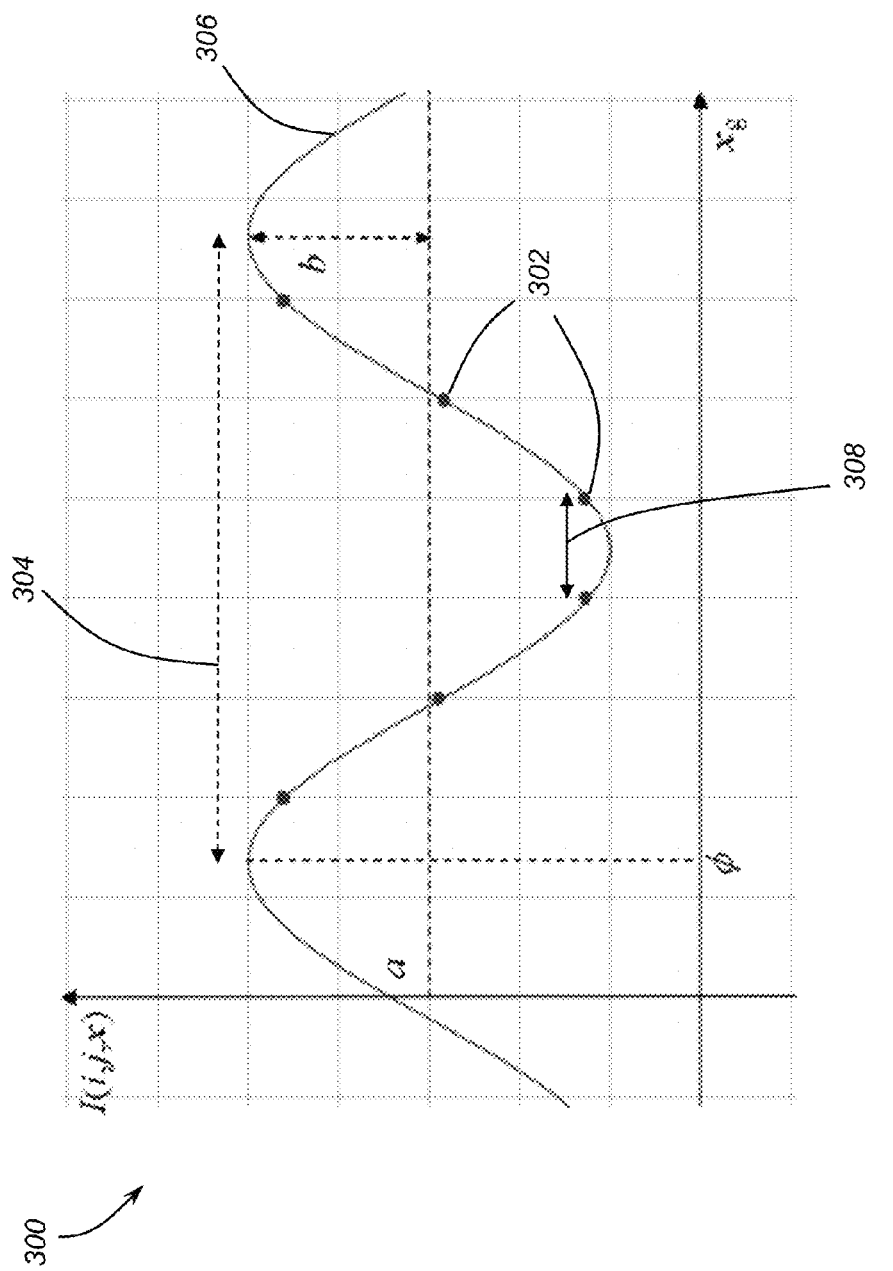
FIG. 3 is an exemplary intensity curve formed by stepping the absorption grating of FIG. 2 in the x direction.

For example, the analyzer grating 226 may be stepped along the x axis over a distance 238 equal to a pitch of the grating 226. At each step the x-ray source 202 may be fired to expose the object 224 via filter 204, collimator 208, and initial source grating 206, comprising a slit size 210 and pitch 212, which generates a more coherent x-ray beam 214 comprising a plurality of x-rays 218 propagating in the direction 236. The x-ray intensity may be detected and measured by the detector 240 comprising pixels 244 each having a size dimension 242. When the stepping is completed, e.g., the distance 238 is traversed by a number of steps with a radiographic image captured at each step, the measured intensity signal at each pixel across the plurality of captured images comprises a sinusoidal shape, as shown in FIG. 3. This is due to the diffractive effect on the x-rays 218 caused by phase grating 216, whereby the x-rays 218 of the x-ray beam 214 are diffracted along paths 230 causing a sinusoidal variation in intensity 232 near the grating 226. By translating the grating 226 along the x axis in equal steps and exposing the object 224 with each step, the variable (sinusoidal) intensity of the x-rays are detected at corresponding pixels 244 of the digital x-ray detector 240. The distance 222 between the grating 206 and the grating 216 as well as the distance 234 between the grating 216 and 226 may be adjusted for optimal image differentiation.

The x-ray source 202 and the digital detector 240, as well as components of the imaging apparatus 200, may communicate with a control and image processing unit 201 over a connected cable or with a wireless transmitter to transmit radiographic image data wirelessly to the control and image processing unit 201. The control and image processing unit 201 may include a processor and electronic memory (not shown) to control operations of the imaging apparatus 200 as described herein by use of programmed instructions. The control and image processing unit 201 may also be used to control activation of the x-ray source 202 during a radiographic exposure, controlling an x-ray tube electric current magnitude, and thus the fluence of x-rays 218 in x-ray beam 214, and the x-ray source voltage, and thus the energy level of the x-rays 218 in x-ray beam 214. The control and image processing unit 201 may transmit image (pixel) data to a monitor based on the radiographic exposure data received from the array photosensitive pixel cells in the detector 240. Taking into account that FIG. 2 is not drawn to an exacting scale, and while only exemplary, the grating pitch 212 of the source grating 206 may be selected at about 50-100 μm; the grating pitch 228 of the phase grating 216 may be selected at about 4 μm; and the grating pitch 238 of the analyzer grating 226 selected at about half that, i.e. about 2 μm, of the phase grating 216.

3. Image Formation

When an open field measurement is conducted (i.e. the object 224 is not present), the signal oscillation curve (or intensity curve) for each of the detector's pixels 244 (i, j), where i and j designate rows and columns of the detector 140 photosensitive elements, may be expressed as $$I_b(i, j, x_g) = a_b(i, j) + b_b(i, j) \cos\left(\frac{2\pi}{p_2} x_g + \phi_b(i, j) + \frac{2\pi}{p_2} n \Delta x_g\right), \quad (7)$$

where a is the average intensity, b is the signal amplitude, $x_g$ is the lateral position of the grating at the $n^{th}$ step of phase stepping ($\Delta x_g$) 308 (see FIG. 3). The minimal number of steps required for successful image reconstruction is preferably three (3). Thus, when the object 224 is scanned, the equation (7) changes to:

$$I_s(i, j, x_g) = \qquad (8)$$
$$T_s(i, j) \cdot \left[ a_b(i, j) + b_b(i, j)\cos\left(\frac{2\pi}{p_2}x_g + \phi_b(i, j) + \phi_s(i, j) + \frac{2\pi}{p_2}n\Delta x_g\right)\right]$$

where $T_s$ is the intensity of, and $\phi_s$ is the change of the phase of, the x-ray beam when it passes through the object.

4. Modeling of Digital Phantom

Figure 4:
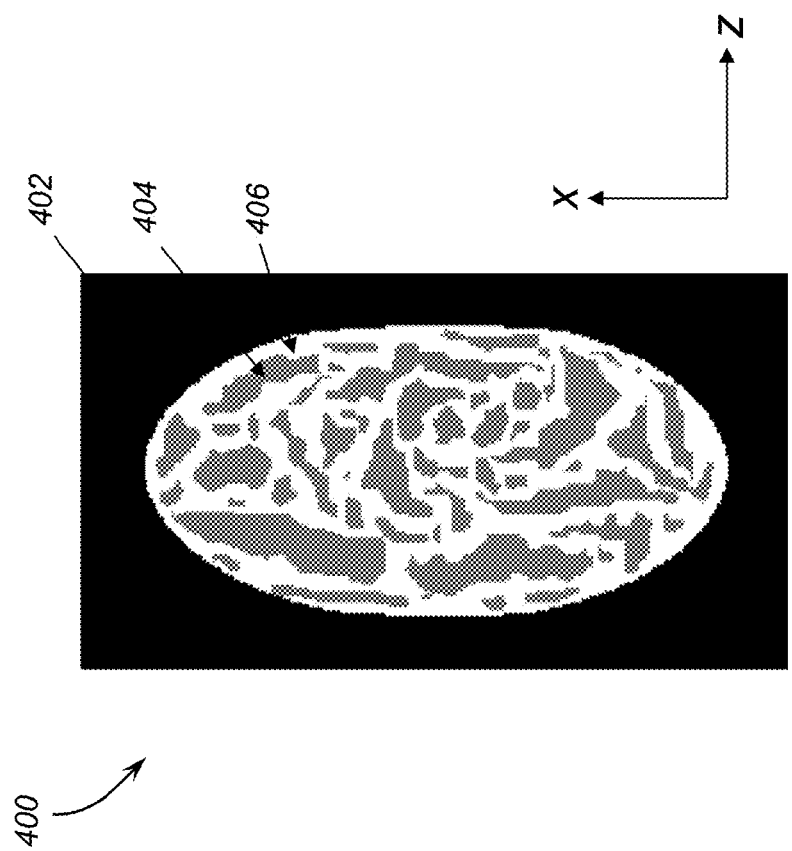
FIG. 4 is a view of the XZ cross section of a digitally modeled compressed breast.

With reference to FIG. 4, a 3D digital phantom of the object was modeled by using 2D digital images 400 of a breast cross section in the XZ plane (in reference to coordinate system 220 shown in FIG. 2). Three different code values were assigned to the areas that represented air 402, glandular 404, and adipose 406 tissues, as shown in FIG. 4. Thus, using equation (6) the XZ cross sectional images of β and δ ("map" images) of the breast may be generated. Then, the map images may used in equation (5) to get the line integrals along the direction of the x-ray beam (i.e., the z axis), which may result in line profiles along the x axis for attenuation and phase shift through the phantom. To model the remaining dimension, the third y axis dimension, it was assumed that the object had exactly the same XZ cross sectional area at any y coordinate. In other words, the x line profiles were stretched along the y axis.

The phase stepping acquisition technique was simulated according to equations (7) and (8). As an example, n=8 steps were simulated, which resulted in 8 reference and 8 sample images. The model of x-ray spectrum propagation through each of the gratings was developed with the help of experimentally measured half-value layers. A cascaded system analysis ("CSA") was performed to model a flat panel charge integrating detector (240) having a 100 µm thick $GdO_2S$ scintillator. The x-ray spectral propagation analysis together with CSA and additional dose measurements allowed modeling realistic noise, which was added to the model images via equations (7) and (8). Furthermore, the data reconstruction was done by employing Fourier analysis technique.

5. Data Reconstruction

The phase stepping acquisition technique requires multiple x-ray exposures each at a different lateral position $x_g$ (i.e., in x-axis) of the analyzer grating 226 (or relative displacement of any of the three gratings with respect to each other), which allows the generation of an intensity plot 300, for example, a cosine (or sine) shaped intensity curve 306 shown in FIG. 3 having a wavelength 304 which represents the output of one pixel (i, j) wherein i, j, represent a column and row index identifying a particular pixel. The six data points 302 on the example plot 300 represent each of six captured radiographic images at each translated step of the analyzer grating 226. Thus, in this example there are six steps and the signal oscillation detected by each pixel of the detector 240 comprises information with respect to an intensity level (absorption) of the captured x-ray (I(i, j, x) vertical axis) and a phase angle ($\phi$(i, j) horizontal axis).

For each pixel (i, j), such a signal oscillation curve (or intensity curve) may be expressed by a Fourier series:

$$I_s(i, j, x_g) \approx a_s(i, j) + b_s(i, j)\cos\left(\frac{2\pi}{p_2}x_g + \phi_s(i, j)\right), \qquad (9)$$

$$I_b(i, j, x_g) \approx a_b(i, j) + b_b(i, j)\cos\left(\frac{2\pi}{p_2}x_g + \phi_b(i, j)\right). \qquad (10)$$

Here, Equation (9) represents the intensity measurement with object present, while Equation (10) refers to measurement without an object, i.e. a reference scan or open field measurement. Applying a Fourier analysis technique, the following images may be obtained:

1) transmission image:

$$T(i, j) = \frac{a_s(i, j)}{a_b(i, j)}, \qquad (11)$$

2) dark-field image:

$$V(i, j) = \frac{b_s(i, j)/a_s(i, j)}{b_b(i, j)/a_b(i, j)}, \qquad (12)$$

3) differential phase contrast image:

$$\left(\frac{\partial \varphi}{\partial x}\right)_{i,j} = \frac{p_2}{\lambda d_n}(\phi_s(i, j) - \phi_b(i, j)), \qquad (13)$$

4) integrated phase contrast image:

$$\varphi_{i,j} = \frac{p_2}{\lambda d_n}\int(\phi_s(i, j) - \phi_b(i, j))dx. \qquad (14)$$

These four images of the object may be derived from the same data set and may be complementary to each other to provide multiple information of the scanned object enabling the visualization of subtle details in the object.

Figure 5C:
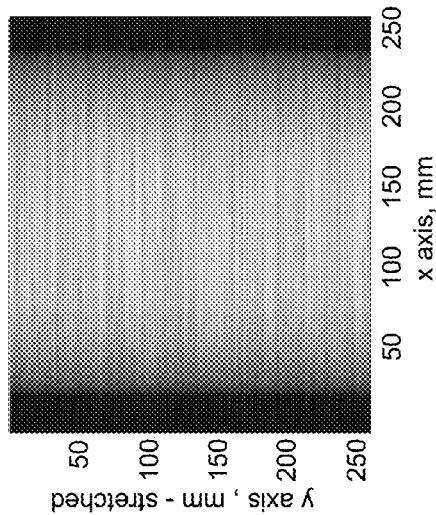
FIGS. 5A-C are reconstructed images of linear attenuation μ·t, differential phase shift φ·t, and integrated phase shift $$\frac{\partial (\varphi \cdot t)}{\partial x},$$
Figure 5B:
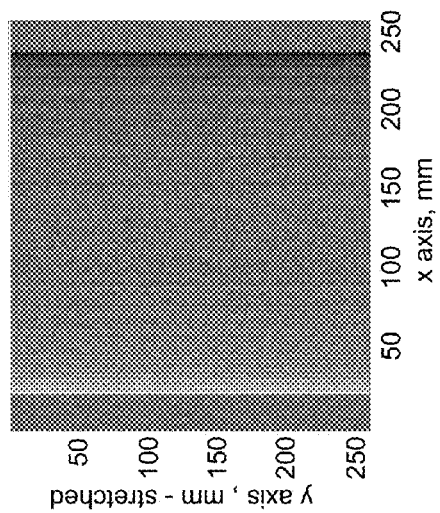
Figure 5A:
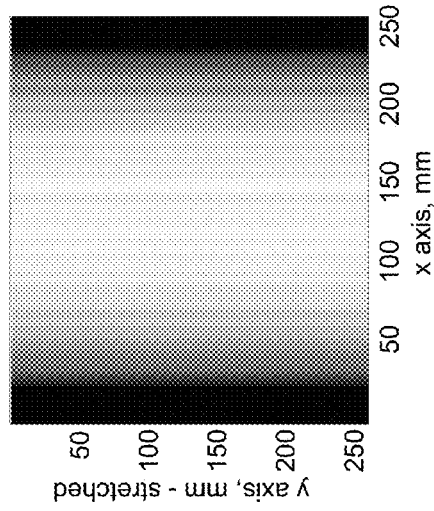

FIGS. 5A-C show examples of reconstructed images of linear attenuation (µ·t) in FIG. 5A, differential phase shift ($\partial(\phi \cdot t)/\partial x$) in FIG. 5B, and integrated phase shift ($\phi \cdot t$) in FIG. 5C. The integrated phase image is a result of integration of $\partial(\phi \cdot t)/\partial x$ in the x direction, i.e.

$$\int \frac{\partial(\varphi \cdot t)}{\partial x} dx.$$

As seen from equations (2), the first and third images, FIGS. 5A and 5C, may be needed for calculating adipose and glandular thickness maps.

Due to a noise in the differential phase shift image, the integrated phase shift image contains multiple streak artifacts in the direction of integration (e.g., x-direction). When such artifacts are present, the precision of breast density measurement may be compromised. Therefore, to get accurate measurements it may be highly important to remove streak artifacts from the integrated phase shift image prior to breast density assessment. The artifact cleaning may involve any type of image denoising algorithms, applied to integrated phase shift image. Alternatively, the phase integration may be performed with a regularization term, which would provide smoothing in the y-axis (or in both x and y axes). Also, denoising algorithms may be applied to any of the three images, for example the linear attenuation (FIG. 5A) and differential phase (FIG. 5B) images prior to integration or regularized integration. An example of regularized integration of the differential phase contrast image is shown in FIG. 6, whereby the streak artifacts are significantly reduced.

FIGS. 7A and 7B show reconstructed images of thickness maps for adipose and glandular tissues, respectively, calculated by using equation (2). FIGS. 8A and 8B shows an example of a profile at y=100 across the x-direction for theoretical (i.e. given in digital phantom) and calculated thickness values of adipose and glandular tissues, respectively. In FIG. 8A, for example, the calculated curves repeat the trend of the theoretical curve, although offset in some parts. Smoothing (or regularized integration) may provide better results, where the match between theoretical and calculated adipose and glandular curves may be improved.

FIG. 9 shows breast density individually estimated for each y profile. Since the projection of the digital phantom was stretched in y direction to simulate the 2D projection of the breast, the breast density values theoretically should be the same for any y profile. This would be true if result images would be noise-free. However, due to noise in the images, the values of the breast density fluctuate around some mean value, which is close to the theoretical prediction. The spread of such fluctuations may be decreased by lowering the noise in the images, which may be done by using a detector with lower noise characteristics, for example CsI detector or Cd—Zn—Te detector.

Breast density, calculated by exemplary system and method embodiments according to this application, may provide rough estimates of breast density, as complementary information to routine breast screening with phase contrast imaging. The scatter may significantly alter the results of breast density calculations, especially for dense breasts. Therefore, a scatter correction may be necessary prior to applying the exemplary system and method embodiments. The present application contemplates methods and program products on any computer readable media for accomplishing its operations. Exemplary embodiments according to the present application may be implemented using an existing computer processor, or by a special purpose computer processor incorporated for this or another purpose or by a hardwired system. Also known in the art may be digital radiographic imaging panels that utilize an array of pixels comprising an x-ray absorbing photoconductor, such as amorphous Selenium (a-Se), and a readout circuit. Since the x-rays may be absorbed in the photoconductor, no separate scintillating screen is required.

It should be noted that while the present description and examples may be primarily directed to radiographic medical imaging of a human or other subject, embodiments of apparatus and methods of the present application may also be applied to other radiographic imaging applications. This includes applications such as non-destructive testing (NDT), for which radiographic images may be obtained and provided with different processing treatments in order to accentuate different features of the imaged subject.

As will be appreciated by one skilled in the art, the present invention may be embodied as a system, method, or computer program product. Accordingly, embodiments of the present invention may be in the form of an entirely hardware embodiment, an entirely software embodiment (including firmware, resident software, stored model data, micro-code, and other suitable encodings) or an embodiment combining software and hardware aspects that may all generally be referred to herein as a "circuit" or "system." Furthermore, the present invention may take the form of a computer program product embodied in a computer-readable storage medium, with instructions executed by one or more computers or host processors. This medium may comprise, for example: magnetic storage media such as a magnetic disk (such as a hard drive or a floppy disk) or magnetic tape; optical storage media such as an optical disc, optical tape, or machine readable bar code; solid state electronic storage devices such as solid state hard drives, random access memory (RAM), or read only memory (ROM); or any other physical device or medium employed to store a computer program. The computer program for performing the method of the present invention may also be stored on computer readable storage medium that may be connected to a host processor by way of the internet or other communication medium.

Those skilled in the art will readily recognize that the equivalent of such a computer program product may also be constructed in hardware. The computer-usable or computer-readable medium could even be paper or another suitable medium upon which executable instructions may be printed, as the instructions may be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that may contain, store, communicate, propagate, or transport computer instructions for use by, or in connection with, an instruction execution system, apparatus, or device.

Exemplary embodiments described herein relate to methods and systems of operating a digital x-ray detector for the purpose of non-invasive or automatic x-ray beam detection. Exemplary embodiments described herein relate to methods and systems of operating a digital x-ray detector using continuously read out of the imaging panel, and the image data monitored to determine when the exposure occurred. Image data may be summed for all captured frames and may be corrected using dark image captures conducted before and after exposed frame acquisition. Exemplary embodiments described herein relate to methods and systems of operating a digital x-ray detector using multi-sample (e.g., two) continuously read out of the imaging panel (e.g., row by row). Exemplary embodiments described herein relate to methods and systems of operating a digital x-ray detector using multi-sample (e.g., two) continuously read out of the imaging panel (e.g., row by row) where the second read out of each row may be used for image correction of at least part of an x-ray exposure image. Exemplary embodiments described herein relate to methods and systems of operating a digital x-ray detector using multi-sample (e.g., two) continuously read out of the imaging panel that have been demonstrated to deliver robust beam sensing and acceptable imaging performance.

While the invention has been illustrated with respect to one or more implementations, alterations and modifications may be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. The term "at least one of" may be used to mean one or more of the listed items may be selected. The term "about" indicates that the value listed may be somewhat altered, as long as the alteration does not result in nonconformance of the process or structure to the illustrated embodiment. Finally, "exemplary" indicates the description may be used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of determining material composition of an object, the method comprising:
   capturing a series of digital radiographic images of the object using an x-ray beam;
   determining an intensity of the captured images of the object;
   determining a phase shift magnitude that occurred in the object using the captured images of the object;
   generating a differential phase shift image of the object;
   generating an integrated phase image of the object;
   determining a difference in material composition of the object based on a combination of the differential phase shift image and the integrated phase image; and
   generating and displaying a radiographic image of the object including separately displaying within the radiographic image of the object glandular and adipose tissue inside the object.

2. The method of claim 1, wherein the step of capturing comprises using a digital detector, the digital detector comprising a plurality of pixels, and wherein the steps of determining the intensity and determining the phase shift magnitude are performed for each pixel.

3. The method of claim 2, wherein the step of capturing comprises positioning a plurality of gratings in a path of the x-ray beam and phase stepping only a first one of the gratings into a different position for capturing each of the radiographic images.

4. The method of claim 3, wherein the step of phase stepping comprises repositioning the first one of the gratings an equal distance for each of a plurality of phase steps, wherein a total distance of the plurality of phase steps is equal to or greater than a pitch magnitude of the first one of the gratings.

5. The method of claim 4, wherein a second one of the gratings comprises a phase grating for generating an interference pattern of the x-ray beam after the x-ray beam has passed through the object, and wherein the pitch magnitude of the first one of the gratings is equivalent to the distance between peaks of the interference pattern.

6. The method of claim 5, wherein the step of capturing the series of radiographic images comprises positioning the first grating behind the second grating and capturing the radiographic images immediately after the x-ray beam has passed through the first grating.

7. The method of claim 5, wherein the pitch magnitude of the first grating is about half of a pitch magnitude of the second grating.

8. The method of claim 5, wherein the step of phase stepping comprises repositioning the first one of the gratings in a direction perpendicular to a direction of the x-ray beam emitted by the x-ray source.

9. The method of claim 8, wherein the step of determining the difference in material composition comprises measuring an intensity of incident x-rays in pixels of at least one of the captured radiographic images.

10. The method of claim 9, wherein the step of determining the difference in material composition comprises determining a phase shift across the captured radiographic images, wherein the pixel values are each correspond to one data point of a sinusoidal shape of the interference pattern.

11. A method of determining material composition of an object, the method comprising:
    capturing a series of digital radiographic images of the object using an x-ray beam emitted by an x-ray source;
    determining an energy intensity of the captured radiographic images of the object;
    determining a magnitude of an x-ray phase shift that occurred in the object using the captured radiographic images of the object;
    generating a differential phase shift image of the object;
    generating an integrated phase image of the object;
    determining a difference in material composition of the object based on a combination of the determined energy intensity and the determined magnitude of the x-ray phase shift; and
    generating and displaying a radiographic image of the object including separately displaying within the radiographic image of the object glandular and adipose tissue inside the object using the differential phase shift image of the object and the integrated phase image of the object.

12. The method of claim 11, wherein the step of capturing comprises using a digital detector, the digital detector comprising a plurality of pixels, and wherein the steps of determining the energy intensity and determining the magnitude of the x-ray phase shift are performed for each pixel.

13. The method of claim 12, wherein the step of capturing comprises positioning a plurality of gratings in a path of the x-ray beam and phase stepping only a first one of the gratings into a different position for capturing each of the radiographic images.

14. The method of claim 13, wherein the step of phase stepping comprises repositioning the first one of the gratings an equal distance for each of the different positions, wherein a total distance of said repositioning the first one of the gratings for each of the different positions is equal to or greater than a pitch magnitude of the first one of the gratings.

15. The method of claim 14, wherein a second one of the gratings comprises a phase grating for generating an interference pattern of the x-ray beam after the x-ray beam has passed through the object, and wherein the pitch magnitude of the first one of the gratings is equivalent to the distance between peaks of the interference pattern.

16. The method of claim 15, wherein the step of capturing the series of radiographic images comprises positioning the first grating behind the second grating in relation to the x-ray source and capturing the radiographic images after the x-ray beam has passed through the first grating.

17. The method of claim 15, wherein the pitch magnitude of the first grating is about half of a pitch magnitude of the second grating.

18. The method of claim 15, wherein the step of phase stepping comprises repositioning the first one of the gratings in a direction perpendicular to a direction of the x-ray beam emitted by the x-ray source.

19. The method of claim 18, wherein the step of determining the difference in material composition comprises measuring an intensity of incident x-rays in pixels of at least one of the captured radiographic images.

20. The method of claim 19, wherein the step of determining the difference in material composition comprises determining a phase shift across the captured radiographic images, wherein the pixel values each correspond to a data point on the interference pattern.

* * * * *